United States Patent [19]

Chenard et al.

[11] Patent Number: 4,723,016

[45] Date of Patent: Feb. 2, 1988

[54] PREPARATION OF ANHYDROUS ORGANIC ACID SALTS

[75] Inventors: Bertrand L. Chenard; Evan D. Laganis, both of Wilmington, Del.

[73] Assignee: E. I. Du Pont de Nemours and Company, Wilmington, Del.

[21] Appl. No.: 828,978

[22] Filed: Feb. 13, 1986

Related U.S. Application Data

[63] Continuation of Ser. No. 625,907, Jun. 29, 1984, abandoned.

[51] Int. Cl.$^4$ .................. C07D 401/00; C07C 51/00
[52] U.S. Cl. ............................. 546/319; 546/327; 260/413; 260/513 R; 549/499; 549/508; 558/87; 558/260; 562/429; 562/583; 562/605; 562/607; 560/190

[58] Field of Search .................. 546/341, 319, 327; 525/330.3, 330.6, 315; 560/190; 260/318, 319, 413 R, 513 R, 502.4 R, 513 F, 505 R, 417; 562/438, 493, 429, 583, 605, 606, 607; 558/87, 260; 549/499, 500, 508

[56] References Cited

U.S. PATENT DOCUMENTS 3,631,161 12/1971 Fan ........................................ 525/342

OTHER PUBLICATIONS

Chem. Abst., 86, 15809v, (1977).
Chem. Abst., 99, 174898h, (1983).

*Primary Examiner*—Christopher Henderson

[57] ABSTRACT

One-step process for preparing anhydrous, organic acid alkali or alkaline earth metal salts by contacting and reacting an organic or polymeric acid fluoride, anhydride or ester and an organic alkali or alkaline earth metal silanolate.

37 Claims, No Drawings

PREPARATION OF ANHYDROUS ORGANIC ACID SALTS

CROSS-REFERENCE TO RELATED APPLICATION

This is a continuation of application Ser. No. 625,907 filed June 29, 1984, and abandoned.

BACKGROUND OF THE INVENTION

1. Field of the Invention

This invention relates to a one-step process for preparing anhydrous organic acid salts.

2. Background

Nametkin et al., Doklady Akad. Nauk S.S.S.R. 87, 233 (1952), C.A. 47, 12281f (1953), disclose the preparation of a silyl ester by reaction of a metal silanolate, for example, triphenylsilyloxysodium, and an acid chloride, for example, acetyl chloride, in refluxing petroleum ether.

Sommer et al., J. Am. Chem. Soc. 86, 3280 (1964), in a study of the stereochemistry of asymmetric silicon, disclose the reaction of a potassium silanolate, for example, α-naphthylphenylmethylsilyloxypotassium and an acid chloride, for example, acetyl chloride, benzoyl chloride or a nitrobenzoyl chloride, to produce the silyl ester. The authors also disclose that the corresponding reaction with tosyl chloride does not yield an isolable silyl ester because the ester reacts with additional potassium silanolate to form a disiloxane.

Birkofer et al., Chem. Ber. 102, 3094 (1969), C.A. 71, 91564s (1969) disclose the reaction of N-methylbenzimidoyl chloride and trimethylsilyloxysodium to produce N,N'-dimethyl-N'-benzoylbenzamidine according to the equations

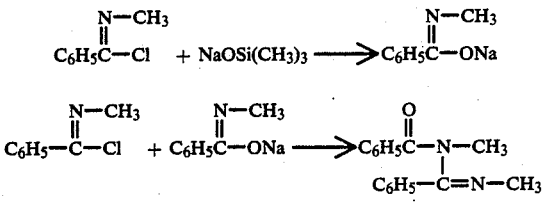

U.S. Pat. No. 3,926,954 discloses a process for preparing salts of carboxylic acids containing a β-lactam group. More specifically, a dimethyl- or trimethylsiloxy ester of a penicillin, a cephalosporin or a 6-aminopenicillanic acid is reacted with a sodium, potassium or calcium salt of phenol or a specific organic acid, alkanol or silanol.

DETAILED DESCRIPTION OF THE INVENTION

For further comprehension of the invention and of the objects and advantages thereof, reference may be made to the following description and to the appended claims in which the various novel features of the invention are more particularly set forth.

The invention resides in a one-step synthesis of anhydrous, organic acid alkali metal or alkaline earth metal salts by contacting under reaction conditions the organic compound of the formula $R(ZX)_k$, or the polymer containing one or more units of the formula $$-C(R'ZX)-$$

or $-(ZO)-$, and the organic alkali metal or alkaline earth metal silanolate of the formula $[(R^1)(R^2)(R^3)SiO]_nM$ wherein:

each Z, independently, is

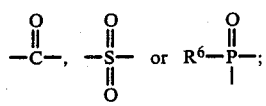

each X, independently, is the monovalent leaving group F or $OR^5$, or: (i)

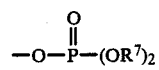

when Z is

or (ii)

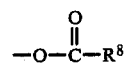

when Z is

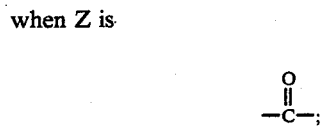

M is alkali or alkaline earth metal;
n is 1 or 2;
k is 1, 2 or 3;
R is selected from a connecting bond, $R^4$ and $OR^4$ wherein $R^4$ is an aliphatic, unsaturated aliphatic, fluorinated aliphatic, alicyclic, aromatic or aliphatic-aromatic hydrocarbon radical which contains up to 30 carbon atoms and which is of valence k, any of said hydrocarbon radicals optionally containing ether oxygen, thioether sulfur or tertiary nitrogen atoms, and/or any of all of said radicals optionally substituted with one or more functional groups that are inert under reaction conditions; preferably, $R^4$ is $C_{1-12}$ alkyl, $C_{1-12}$ fluorinated alkyl or $C_{6-10}$ aryl;
R' is selected from a connecting bond, R" and OR" wherein R" is a divalent aliphatic or fluorinated aliphatic hydrocarbon radical containing up to 30 carbon atoms, any of said radicals optionally containing ether oxygen;
each of $R^1$, $R^2$, and $R^3$ is independently selected from H, provided at least one of these groups is not H, $C_{1-10}$ alkyl, $C_{1-10}$ oxyalkyl and $C_{6-10}$ aryl and alkaryl; preferably, each $R^1$, $R^2$ and $R^3$ is independently selected from $C_{1-3}$ alkyl; more preferably, each of $R^1$, $R^2$ and $R^3$ is methyl;
each $R^5$, independently, is a $C_{1-30}$ alkyl or fluorinated alkyl, $C_{2-30}$ alkenyl or alkynyl, $C_{3-8}$ cycloalkyl, or $C_{6-30}$ aryl, aralkyl or alkaryl radical, or a polymeric hydrocarbon radical containing at least 30 carbon atoms, any of said alkyl, fluorinated alkyl, alkenyl, alkynyl, cycloalkyl or polymeric radicals optionally containing ether oxygen, thioether sulfur or tertiary nitrogen atoms, or any of all of said radicals optionally substituted with one or more functional groups that are inert under reaction conditions; preferably, each $R^5$, independently, is $C_{1-12}$ alkyl or $C_{6-12}$ aryl or aralkyl;

each $R^6$, independently, is $R^7$ or $OR^7$;

each $R^7$, independently, is $C_{1-20}$ alkyl or $C_{6-20}$ aryl, alkaryl or aralkyl, preferably, $C_{1-10}$ alkyl or $C_{6-10}$ aryl; and each $R^8$, independently, is $C_{1-12}$ alkyl, preferably $C_{1-4}$ alkyl.

By "monovalent leaving group" is meant the monovalent atom or radical, of symbol X, within the starting organic compound or polymer which is displaced in the reaction with silanolate. Halogen atoms other than F have been found to be unsuitable leaving groups.

By "reaction conditions" is meant in an anhydrous inert atmosphere, such as nitrogen, helium or argon, at a temperature of about −80° C. to about 200° C., preferably from about 10° C. to about 120° C., most preferably room temperature.

Use of an inert dry solvent is desirable but not essential, except when the reactants are solids or are mutually insoluble. The reactants must be at least partly soluble in the solvent employed. A liquid reactant may serve as a solvent provided the other reactant is at least partly soluble therein. Preferred solvents include tetrahydrofuran (THF), ether, toluene, methylene chloride, and o-dichlorobenzene.

The reactants are mixed in a molar ratio ($R(ZX)_k$:silanolate), or a ratio of the number of equivalents of

or —(ZO)— to moles of silanolate, of about 3:1 to at least about 1:3, preferably about 2:1 to about 1:40, more preferably about 2:1 to about 1:10, the ratio of choice depending at least in part on the value of k and the valence of M; the following equations are illustrative:

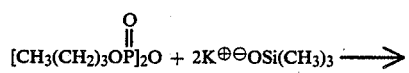

1.

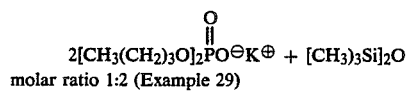

molar ratio 1:2 (Example 29)

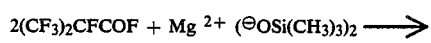

2.

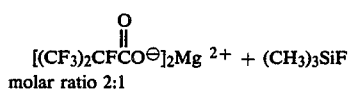

molar ratio 2:1

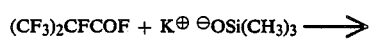

3.

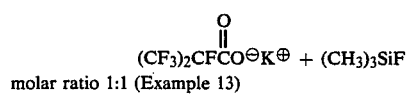

molar ratio 1:1 (Example 13)

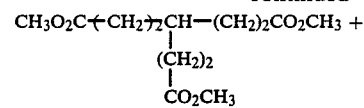

4.

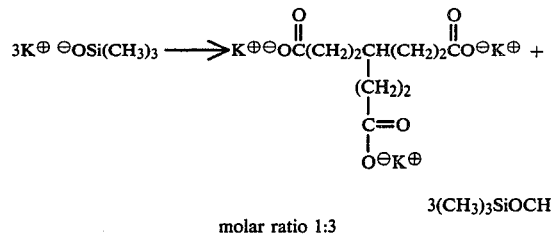

molar ratio 1:3

Organic compounds of formula $R(ZX)_k$ which are useful in the invention process include, but are by no means limited to, aliphatic and aromatic esters, which may be fluorinated; as illustrations: ethyl perfluoropropionate, methyl 4-(4'-nitrophenyl)-2-fluoro-3-oxa-2-trifluoromethylbutyrate, benzyl benzoate and diethyloxalate; heterocyclic esters, such as alkyl 2-furoates and alkyl nicotinates; fluorinated aliphatic and aromatic acyl fluorides, such as perfluoro-2-methyl-3-oxapentanoyl fluoride, 2,2-bis(trifluoromethyl)decanoyl fluoride and perfluoro-3-phenoxypropanoyl fluoride; aliphatic and aromatic sulfonyl fluorides, such as perfluoro-3-oxapentanesulfonyl fluoride and o-, m- and p-toluenesulfonyl fluoride; aliphatic fluorophosphates and phosphates; aliphatic and aromatic phosphinates; mixed function compounds, such as 4-carbomethoxyperfluoro-2-methyl-3-oxapentanoyl fluoride; anhydrides, such as acetic- and propionic anhydride. Polymers containing structural units

or —(ZO)— include, but are not limited to, polyesters, such as copolymers of 2-methylene-1,3-dioxepane and ethylene, poly(ethylene terephthalate) and poly(ethylene adipate); polymers containing pendant ester functions, such as poly(acrylates), poly(methacrylates) and fluorinated poly(ether esters) which contain structural units of the formula

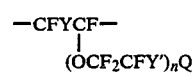

wherein: Y is —F or —Cl; Y' is —F or —CF$_3$; Q is —COF, —CO$_2$R'", —SO$_2$F, or —P(O)(Q')$_2$; Q' is —F or —OR'"; R'" is $C_{1-10}$ alkyl; and n is an integer and is at least 1. Any of the polymers may contain substituents and/or end groups which are inert under reaction conditions.

If the product of the invention process precipitates, it may easily be isolated by filtration under an inert atmosphere. Product salts which do not precipitate can be isolated by concentrating the reaction mixture under vacuum.

Functional groups (in R and $R^5$) that are inert under reaction conditions include but are not limited to F, Cl, Br, NR$_2$'", SR'" and OR'" wherein R'" is $C_{1-10}$ alkyl. Starting compounds containing highly acidic α-hydrogen atoms, such as acetoacetic esters, should be avoided as the silanolate acts as a base, attacking and removing the acidic proton.

The anhydrous acid salts prepared by the process of the invention are useful in a variety of applications, for example, as surfactants and detergents (see "Surfactants, Detergents, and Sequestrants: Developments Since 1979", J. I. Distasio, Ed., Noyes Data Corp., Park Ridge, N.J., 1981 and S. J. Gutcho, "Surfactants and Sequestrants: Recent Advances", Noyes Data Corp., Park Ridge, N.J., 1977); as intermediates to fluoroolefin monomers used in fluoroplastics and fluoroelastomers: U.S. Pat. No. 3,326,984 and R. D. Chambers, "Fluorine in Organic Chemistry", John Wiley & Sons, N.Y. 1973, p. 119); and as pharmaceutical intermediates and end products: U.S. Pat. No. 3,926,954.

The salts prepared by the process of the invention are conventionally prepared in the art by neutralizing an aqueous solution of the corresponding acid with a standardized solution of metal hydroxide. Isolation of the acid salt in anhydrous form from the aqueous medium can be difficult and tedious. The process of the invention offers the following advantages over conventional methods:

(1) Nonaqueous conditions are employed.
(2) The anhydrous salts are easily isolated by simple filtration or evaporation of the reaction mixture.
(3) The process frequently yields analytically pure salts directly.
(4) The by-products are easily removed.

In the following examples, temperatures are reported in degrees Celsius; $^1$H NMR spectroscopic chemical shifts are reported in parts per million ($\delta$) downfield from tetramethylsilane (TMS) internal standard, in organic solvents, or, in aqueous solutions, in parts per million ($\delta$) downfield from 2,2-dimethyl-2-silapentane-5-sulfonate sodium salt (DSS) as internal standard, or relative to D$_2$O/H$_2$O (4.61 ppm vs. TMS) as standard; $^{19}$F NMR chemical shifts are reported in parts per million upfield from Freon®-11 internal standard. The products were analyzed immediately after isolation without further purification.

EXAMPLE 1

Sodium perfluorobutyrate

Methyl perfluorobutyrate (12.81 g, 56 mmol) was added dropwise to a stirred solution of sodium trimethylsilanolate (6.3 g, 56 mmol) in dry ether (300 mL) at room temperature under nitrogen. The reaction mixture was stirred overnight. The solid was filtered under nitrogen, washed with dry ether, and dried under a stream of nitrogen to afford sodium perfluorobutyrate (11.1 g, 84% yield) as a white solid: $^{19}$F NMR (D$_2$O) $\delta$ −79.6 (t, J=8 Hz, CF$_3$—, 3F), −117.2 (q, J=8 Hz, CF$_3$CF$_2$CF$_2$—, 2F), −126.2 ppm (s, CF$_3$CF$_2$—, 2F). Anal. Calcd. for C$_4$F$_7$NaO$_2$: C, 20.36; F, 56.35; Na, 9.74. Found: C, 20.84, 20.61, 20.58; F, 56.68, 53.24; Na, 9.89, 9.65.

If methyl stearate, methyl tetracosanoate or methyl triacontanoate is substituted for methyl perfluorobutyrate in Example 1, the product is, respectively, sodium stearate, sodium tetracosanoate or sodium triacontanoate.

EXAMPLE 2

Potassium perfluoropropionate

The procedure of Example 1 was followed using ethyl perfluoropropionate (4.8 g, 25 mmol), potassium trimethylsilanolate (3.2 g, 25 mmol), and dry ether (150 mL). Potassium perfluoropropionate (4.7 g, 93% yield) was isolated as a white solid: $^{19}$F NMR (D$_2$O) $\delta$ −79.5 (m, CF$_3$, 3F), −117.5 (m, CF$_2$, 2F). Anal. Calcd. for C$_3$F$_5$KO$_2$: C, 17.83; F, 47.00; K, 19.35. Found: C, 17.52; F, 46.83; K, 19.24.

EXAMPLE 3

Potassium 4-(4′-nitrophenyl)-2-fluoro-3-oxa-2-trifluoromethylbutyrate

The procedure of Example 1 was followed using methyl 4-(4′-nitrophenyl)-2-fluoro-3-oxa-2-trifluoromethylbutyrate (3.11 g, 10.0 mmol), potassium trimethylsilanolate (1.29 g, 10.0 mmol), dry ether (80 mL), and a 2 h reaction time. Potassium 4-(4′-nitrophenyl)-2-fluoro-3-oxa-2-trifluoromethylbutyrate (2.9 g, 87% yield) was isolated as a tan solid: $^1$H NMR (D$_2$O) $\delta$ 4.9 (s, CH$_2$, 2H), 7.6 (d, J$_{HH}$=8.5 Hz, Ar—H's, 2H), 8.2 ppm (d, J$_{HH}$=8.5 Hz, Ar—H's, 2H); $^{19}$F NMR (D$_2$O) $\delta$ −79.1 (d, J$_{FF}$=3.4 Hz, CF$_3$, 3F), −125.0 ppm (q, J$_{FF}$=3.4 Hz, CF, 1F). Anal. Calcd. for C$_{10}$H$_6$F$_4$KNO$_5$: C, 35.83; H, 1.80; N, 4.18; F, 22.67. Found: C, 34.70, 34.46; H, 1.87, 1.68; N, 3.8; F, 20.85, 20.69.

EXAMPLE 4

Sodium benzoate

The procedure of Example 1 was followed using benzyl benzoate (4.8 mL, 5 mmol), sodium trimethylsilanolate (2.82 g, 25 mmol), dry tetrahydrofuran (100 mL), and 6.25 h of heating at reflux. The reaction mixture was cooled to room temperature and sodium benzoate (2.32 g, 64% yield) was isolated as a white solid: $^1$H NMR (D$_2$O) $\delta$ 7.0–8.0 ppm (m, Ar—H's, 5H). Anal. Calcd. for C$_7$H$_5$NaO: C, 58.34; H, 3.50; Na, 15.95. Found: C, 57.99, 57.94; H, 3.80, 3.83; Na, 16.38, 16.60.

EXAMPLE 5

Potassium benzoate

The procedure of Example 1 was followed using benzyl benzoate (9.6 mL, 50 mmol), potassium trimethylsilanolate (6.42 g, 50 mmol), dry ether (150 mL), and a 2 h reaction mixture. Potassium benzoate (5.9 g, 73% yield) was isolated as a white solid: $^1$H NMR (D$_2$O) $\delta$ 7.1–8.0 ppm (m, Ar—H's, 5H). Anal. Calcd. for C$_7$H$_5$KO$_2$: C, 52.48; H, 3.15; K, 24.61. Found: C, 50.53, 50.76; H, 3.40, 3.21; K, 25.60, 25.50.

EXAMPLE 6

Lithium heptanoate

The procedure of Example 1 was followed using methyl heptanoate (5 mL, 30.2 mmol), lithium trimethylsilanolate (2.90 g, 30.2 mmol), dry toluene (50 mL) and 2.5 h of heating at reflux. Lithium heptanoate (2.1 g, 51% yield) was isolated as a white solid: $^1$H NMR (D$_2$O) $\delta$ 0.7 (t, J=5.3 Hz, CH$_3$, 3H), 0.9–1.7 (m, CH$_2$, 8H), 2.1 ppm (t, —CH$_2$CO$_2^-$ Li$^+$, J=7.2 Hz, 2H). Anal. Calcd. for C$_7$H$_{13}$LiO$_2$: C, 61.77; H, 9.63; Li, 5.10. Found: C, 59.84, 59.89; H, 9.47, 9.47; Li, 5.01.

EXAMPLE 7

Potassium 4-chlorobenzoate

The procedure of Example 1 was followed using methyl 4-chlorobenzoate (13.65 g, 80 mmol), potassium trimethylsilanolate (10.26 g, 80 mmol), dry ether (500 mL) and a 4 h reaction time. Potassium 4-chlorobenzoate (13.1 g, 84% yield) was isolated as a white solid: $^1$H NMR (D$_2$O, DSS, 80 MHz) δ 7.68 ppm (ABq, Δν$_{1-3}$=29 Hz, J=8.5 Hz, Ar—H's, 4H). Anal. Calcd. for C$_7$H$_4$ClKO$_2$: C, 43.19; H, 2.07. Found: C, 43.27; H, 2.33.

EXAMPLE 8

Sodium 4-chlorobenzoate

The procedure of Example 1 was followed using methyl 4-chlorobenzoate (4.55 g, 26.6 mmol), sodium trimethylsilanolate (2.99 g, 26.6 mmol), dry toluene (150 mL), and 4 h of heating at 80°. Sodium 4-chlorobenzoate (4.50 g, 86% yield) was isolated as a white solid: $^1$H NMR (D$_2$O, DSS, 80 MHz) δ 7.65 ppm (ABq, Δν$_{1-3}$=29 Hz, J=8 Hz, Ar—H's, 4H).

EXAMPLE 9

Lithium 4-chlorobenzoate

The procedure of Example 1 was followed using methyl 4-chlorobenzoate (4.3 g, 25.2 mmol), lithium trimethylsilanolate (2.42 g, 25.2 mmol), and dry toluene (100 mL) and overnight heating at reflux. Lithium 4-chlorobenzoate (1.9 g, 46% yield) was isolated as a white solid: $^1$H NMR (D$_2$O) δ 7.4 (ABq, Δν$_{1-3}$=31 Hz, J=9 Hz, Ar—H's, 2 H). This solid was contaminated with a small amount of lithium trimethylsilanolate.

EXAMPLE 10

Potassium benzoate

The procedure of Example 1 was followed using phenyl benzoate (3.96 g, 20 mmol), potassium trimethylsilanolate (2.56 g, 20 mmol), dry tetrahydrofuran (50 mL), and a 5 h reaction time. Potassium benzoate (2.37 g, 74% yield) was isolated as a white solid: $^1$H NMR (D$_2$O, DSS, 80 MHz) δ 7.4–8.0 (m, Ar—H's, 5H). Anal. Calcd. for C$_7$H$_5$KO$_2$: C, 52.48; H, 3.15; K, 24.41, Found: C, 50.28, 50.15, 52.45; H, 3.28, 3.36, 3.24; K, 24.80.

EXAMPLE 11

Potassium 2-furoate

The procedure of Example 1 was followed using methyl 2-furoate (2.52 g, 20 mmol), potassium trimethylsilanolate (2.56 g, 20 mmol), dry tetrahydrofuran (50 mL), and a 5 h reaction time. Potassium 2-furoate (2.72 g, 90% yield) was isolated as a light brown solid: $^1$H NMR (D$_2$O, DSS) δ 6.55 (m, Ar—H, 1H), 7.0 (m, Ar—H, 1H) and 7.6 ppm (m, Ar—H, 1H). Anal. Calcd. for C$_5$H$_3$KO$_3$: C, 39.99; H, 2.01; K, 26.04. Found: C, 37.22, 37.41, 40.26; H, 2.33, 2.19, 2.34; K, 26.22.

EXAMPLE 12

Potassium nicotinate

The procedure of Example 1 was followed using methyl nicotinate (2.74 g, 20 mmol), potassium trimethylsilanolate (2.56 g, 20 mmol), dry tetrahydrofuran (50 mL), and a 5 h reaction time. Potassium nicotinate (2.93 g, 90% yield) was isolated as a white solid: $^1$H NMR (D$_2$O, DSS) δ 7.55 (ddd, J=1.0, 5.3, 8.3 Hz, Ar—H, 1H), 8.25 (dt, J=1.9, 8.3, Ar—H, 1H), 8.93 ppm (m, Ar—H, 1H). Anal. Calcd. for C$_6$H$_4$KNO$_2$: C, 44.70; H, 2.50; N, 8.96; K, 24.26. Found: C, 42.28, 42.51, 44.97; H, 2.95, 2.74, 2.83; N, 8.54; K, 24.57.

EXAMPLE 13

Potassium perfluoroisobutyrate

Perfluoroisobutyryl fluoride (17.76 g, 82 mmol) was distilled into a 3-neck flask (equipped with a cold finger condenser, mechanical stirrer and a nitrogen inlet) containing a slurry of potassium trimethylsilanolate (10.26 g, 80 mmol) in dry ether (500 mL). The mixture was stirred 3 h at room temperature with the condenser maintained at −40°; then it was cooled to −40° and stirred overnight. The solid was filtered under nitrogen, washed with dry ether, and dried under a stream of nitrogen to afford potassium perfluoroisobutyrate (12.29 g, 61% yield) as a white solid: $^{19}$F NMR (D$_2$O) δ −72.2 (d, J=7.5 Hz, CF$_3$, 6F), −171.8 ppm (sp, J=7.5 Hz, CF, 1F). Anal. Calcd. for C$_4$F$_7$KO$_2$: C, 19.05; F, 52.75. Found: C, 19.12; F, 52.70.

EXAMPLE 14

Potassium perfluoro-2-methyl-3-oxahexanoate

The procedure of Example 1 was followed using perfluoro-2-methyl-3-oxahexanoyl fluoride (16.6 g, 50 mmol), potassium trimethylsilanolate (6.41 g, 50 mmol), and dry ether (300 mL). Potassium perfluoro-2-methyl-3-oxahexanoate (12.3 g initially and 0.9 g by concentrating the filtrate under vacuum; total: 13.2 g, 72% yield) was isolated as a white solid: $^{19}$F NMR (D$_2$O) δ −81.0

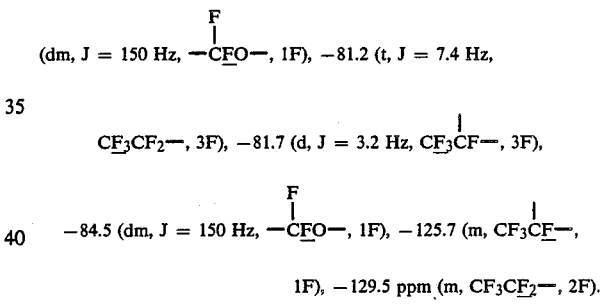

Anal. Calcd. for C$_6$F$_{11}$KO$_3$: C, 19.58; F, 56.77; K, 10.62. Found: C, 18.48, 18.59; F, 55.69, 55.43; K, 11.39, 11.50.

EXAMPLE 15

Sodium perfluoro-2-methyl-3-oxahexanoate

The procedure of Example 1 was followed using perfluoro-2-methyl-3-oxahexanoyl fluoride (33.2 g, 0.1 mol) sodium trimethylsilanolate (11.2 g, 0.1 mol), and dry ether (600 mL). The product was isolated by distilling off approximately two-thirds of the ether, adding pentane (200 mL) and then filtering. Sodium perfluoro-2-methyl-3-oxahexanoate (23.1 g, 66% yield) was isolated as a white solid: $^{19}$F NMR (D$_2$O) δ −79.8

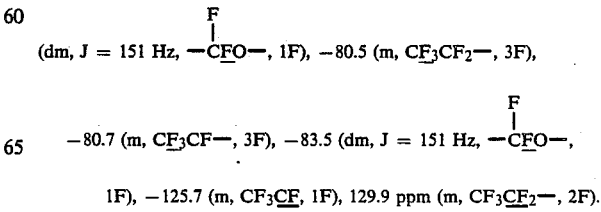

EXAMPLE 16

Sodium perfluoro-2-methyl-3-oxahexanoate

The procedure of Example 1 was followed using perfluoro-2-methyl-3-oxahexanoyl fluoride (16.6 g, 50 mmol), sodium trimethylsilanolate (5.6 g, 50 mmol), dry o-dichlorobenzene (200 mL), and 1 h at room temperature followed by rapid heating to 150°. Sodium perfluoro-2-methyl-3-oxahexanoate (13.6 g, 77% yield) was isolated as a white solid: The $^{19}F$ NMR data were the same as reported in Example 15.

EXAMPLE 17

Sodium perfluoro-2-methyl-3-oxahexanoate

The procedure of Example 1 was followed using perfluoro-2-methyl-3-oxahexanoyl fluoride (16.6 g, 50 mmol), sodium trimethylsilanolate (5.6 g, 50 mmol), and dry tetrahydrofuran (100 mL), and a 2 h reaction time. Sodium perfluoro-2-methyl-3-oxahexanoate (12.2 g, 69% yield) was isolated as a white solid: The $^{19}F$ NMR data were the same as reported in Example 15.

EXAMPLE 18

Sodium perfluoro-2-methyl-3-oxahexanoate

The procedure of Example 1 was followed using perfluoro-2-methyl-3-oxahexanoyl fluoride (33.2 g, 0.1 mol), sodium trimethylsilanolate (11.2 g, 0.1 mol), dry toluene (200 mL), and 1.5 h of heating at reflux. Sodium perfluoro-2-methyl-3-oxahexanoate (23.1 g, 66% yield) was isolated as a white solid: The $^{19}F$ NMR data were the same as reported in Example 15. Anal. Calcd. for $C_6F_{11}NaO_3$: C, 19.77; H, 57.33; Na, 7.63. Found: C, 19.56; H, 56.93; Na, 7.80.

EXAMPLE 19

Lithium perfluoro-2-methyl-3-oxahexanoate

The procedure of Example 1 was followed using perfluoro-2-methyl-3-oxahexanoyl fluoride (16.6 g, 50 mmol) lithium trimethylsilanolate (4.80 g, 50 mmol), and dry ether (300 mL). The product was isolated by concentrating the filtrate under vacuum. An ether solvate of lithium perfluoro-2-methyl-3-oxahexanoate (13.6 g) was isolated as a waxy white solid: $^1H$ NMR (acetone-$d_6$) δ 1.1 (t, $J_{HH}$=7 Hz, $CH_3$, 6H), 3.4 ppm (q, $J_{HH}$=7 Hz, $CH_2$, 4H); $^{19}F$ NMR (acetone-$d_6$) δ −80.6

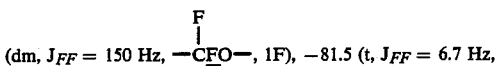(dm, $J_{FF}$ = 150 Hz, −C$\underline{F}$O—, 1F), −81.5 (t, $J_{FF}$ = 6.7 Hz,

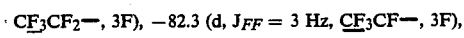C$\underline{F}_3$CF$_2$—, 3F), −82.3 (d, $J_{FF}$ = 3 Hz, C$\underline{F}_3$CF—, 3F),

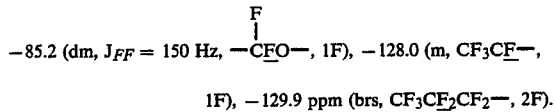−85.2 (dm, $J_{FF}$ = 150 Hz, −C$\underline{F}$O—, 1F), −128.0 (m, CF$_3$C$\underline{F}$—, 1F), −129.9 ppm (brs, CF$_3$C$\underline{F}_2$CF$_2$—, 2F).

EXAMPLE 20

Sodium 2,2-bis(trifluoromethyl)decanoate

The procedure of Example 1 was followed using 2,2-bis(trifluoromethyl)decanoyl fluoride (6.11 g, 19.7 mmol), sodium trimethylsilanolate (2.21 g, 19.7 mmol) and dry ether (20 mL). The product, sodium 2,2-bis(trifluoromethyl)decanoate, was isolated as a waxy solid (5.5 g, 85% yield) by concentrating the filtrate under vacuum: $^1H$ NMR (CDCl$_3$) δ 0.88 (m, CH$_3$, 3H), 1.30 (m, CH$_2$, 12H), 2.10 ppm (m, C$\underline{H}_2$, 2H); $^{19}F$ NMR (D$_2$O/acetone) δ −62.0 ppm (brs, CF$_3$,6F). Anal. Calcd. for $C_{12}H_{17}F_6NaO_2$: C, 43.64; H, 5.19; F, 34.52. Found: C, 44.34; H, 5.10; F, 35.58.

EXAMPLE 21

Potassium perfluoro-3-oxapentanesulfonate

The procedure of Example 1 was followed using perfluoro-3-oxapentanesulfonyl fluoride (7.95 g, 25 mmol), potassium trimethylsilanolate (3.2 g, 25 mmol) and dry tetrahydrofuran (100 mL) while heating at reflux for 1.5 h. Potassium perfluoro-3-oxapentanesulfonate (3.79 g initially and 1.74 g by concentrating the filtrate under vacuum; total 5.53 g, 65% yield) was isolated as a white solid: $^{19}F$ NMR (fluorotrichloromethane) δ −79.4 (m, C$\underline{F}_2$, 2F), −83.2 (s, C$\underline{F}_3$, 3F), −84.9 (m, C$\underline{F}_2$, 2F), −115.0 ppm (m, C$\underline{F}_2$, 2F); Positive ion Fast Atom Bombardment MS (Glycerol matrix, Cs$^\oplus$ ion bombardment) m/e 393, 747, 1101, 1455, 1809 for M+K$^\oplus$ to M$_5$+K$^\oplus$.

EXAMPLE 22

Sodium perfluoro-3-oxapentanesulfonate

Perfluoro-3-oxapentanesulfonyl fluoride (7.95 g, 25 mmol) was added quickly by syringe to a stirring slurry of sodium trimethylsilanoate (2.80 g, 25 mmol) in dry tetrahydrofuran (150 mL) cooled to 15° under nitrogen, giving rise to a 10°-15° exotherm. The reaction mixture was stirred overnight at room temperature before adding hexane (100 mL), but no precipitate formed. The resulting solution was concentrated under vacuum and the residue was triturated with hexane (100 mL) and filtered under nitrogen. The recovered solid was washed with hexane and dried under a nitrogen stream. Sodium perfluoro-3-oxapentanesulfonate (6.09 g, 72% yield) was isolated as a white solid: $^{19}F$ NMR (chlorotrifluoromethane) δ −79.8 (m, C$\underline{F}_2$, 2F), −84.0 (m, CF$_3$, 3F), −85.6 (m, C$\underline{F}_2$, 2F), −115.4 (m, CF$_2$, 2F), −119.3 ppm (brs, impurity): Positive ion Fast Atom Bombardment MS (Glycerol matrix, Cs$^\oplus$ ion bombardment) m/e 361, 699, 1037, 1375, 1713 for M+Na$^\oplus$ to M$_5$+Na$^\oplus$.

EXAMPLE 23

Potassium perfluorohexanesulfonate

The procedure of Example 1 was followed using perfluorohexanesulfonyl fluoride (7.9 g, 19.6 mmol), potassium trimethylsilanolate (2.52 g, 19.6 mmol), dry ether (150 mL), and a reaction time of nine days. Potassium perfluorohexanesulfonate (4.6 g, 53% yield) was isolated as a white solid: $^{19}F$ NMR (methanol) δ −81.1 (m, −CF$_3$−, 3F), −114.4 (m, −CF$_2$SO$_3^\ominus$, 2F), −120.6 (m, −CF$_2$CF$_2$SO$_3^\ominus$, 2F), −121.7 (m, −CF$_2$(CF$_2$)$_2$SO$_3^\ominus$, 2F), −122.6 (m, CF$_3$CF$_2$CF$_2$, 2F), 126.1 ppm (m, CF$_3$C$\underline{F}_2$—, 2F).

EXAMPLE 24

Lithium perfluorooctanesulfonate

The procedure of Example 1 was followed using perfluorooctanesulfonyl fluoride (11.8 g, 23.5 mmol), lithium trimethylsilanolate (2.25 g, 23.4 mmol), and dry tetrahydrofuran (150 mL). The product, lithium perfluorooctanesulfonate (6.6 g, 55% yield), was isolated as a white solid by concentrating the filtrate under vacuum: $^{19}$F NMR (tetrahydrofuran) δ −81.2 (t, J=8.5 Hz, C$\underline{F}$$_3$—, 3F), −114.6 (m, —C$\underline{F}$$_2$CO$_2$⊖, 2 F), −120.6 (m, —C$\underline{F}$$_2$, 2F), −121.7 (m, C$\underline{F}$$_2$, 6F), −122.7 (m, C$\underline{F}$$_2$, 2F), −126.2 ppm (m, CF$_3$C$\underline{F}$$_2$, 2F).

EXAMPLE 25

Potassium perfluorohexanesulfonate

The procedure of Example 1 was followed using perfluorohexanesulfonyl fluoride (7.90 g, 19.6 mmol), potassium trimethylsilanolate (2.20 g, 17.1 mmol), and dry toluene (50 mL), while heating at 40° for 3.5 h. Potassium perfluorohexanesulfonate (4.9 g, 65% yield) was isolated as a white solid: $^{19}$F NMR (methanol) data were closely similar to those reported in Example 23.

EXAMPLE 26

Potassium α-toluenesulfonate

The procedure of Example 1 was followed using α-toluenesulfonyl fluoride (2.0 g, 11.5 mmol) in dry tetrahydrofuran (15 mL), potassium trimethylsilanolate (1.48 g, 11.5 mmol) and dry tetrahydrofuran (45 mL), and 2 h of heating at reflux. Potassium α-toluenesulfonate (1.41 g, 58% yield) was isolated as a white solid: $^1$H NMR (D$_2$O) δ 4.1 (s, C$\underline{H}$$_2$, 2H), 7.4 ppm (s, Ar—$\underline{H}$'s, 5H).

EXAMPLE 27

Potassium diethylphosphate

The procedure of Example 1 was followed except that diethylfluorophosphate (0.9 mL, 6.4 mmol) was added by syringe to a slurry of potassium trimethylsilanolate (0.82 g, 6.4 mmol) in dry ether (25 mL) and a 5 h reaction time was used. Potassium diethylphosphate (0.67 g, 54% yield) was isolated as a tan solid: $^1$H NMR (D$_2$O, DSS) δ 1.2 (t, J=6.9 Hz, C$\underline{H}$$_3$, 6H), 3.9 (q, J=6.9 Hz, C$\underline{H}$$_2$, 4H).

EXAMPLE 28

Potassium dimethylphosphate

The procedure of Example 1 was followed except that trimethylphosphate (2.93 mL, 25 mmol) was added by syringe to a slurry of potassium trimethylsilanolate (3.2 g, 25 mmol) in dry ether (100 mL), and a 5 h reaction time was used. Potassium dimethylphosphate (2.98 g, 72% yield) was isolated as a tan solid: $^1$H NMR (D$_2$O, DSS) δ 3.47 ppm (d, J$_{HP}$=10.9 Hz, C$\underline{H}$$_3$). Anal. Calcd. for C$_2$H$_6$KO$_4$P: C, 14.63; H, 3.68; P, 18.87. Found: C, 14.98; H, 3.89; P, 18.02.

EXAMPLE 29

Potassium dibutylphosphate

The procedure of Example 1 was followed using tetrabutylpyrophosphate (4 mL, 10.5 mmol) in dry tetrahydrofuran (10 mL), potassium trimethylsilanolate (2.68 g, 21 mmol) in dry tetrahydrofuran (50 mL), and a 24 h reaction time. The product, potassium dibutylphosphate (4.46 g, 90% yield), was isolated as a white solid by concentrating the filtrate under vacuum: $^1$H NMR (D$_2$O, DSS) δ 0.8–1.05 (dist. t, C$\underline{H}$$_3$, 6H), 1.18–1.8 (m, C$\underline{H}$$_2$, 8H), 3.74–4.0 (q, C$\underline{H}$$_2$, 4$\overline{H}$). Anal. Calcd. for C$_8$H$_{18}$KO$_4$P: C, 38.70; H, 7.31. Found: C, 38.63; H, 7.38.

EXAMPLE 30

Potassium diphenylphosphinate

The procedure of Example 1 was followed adding neat solid phenyl diphenylphosphinate (5.88 g, 20 mmol) to a slurry of potassium trimethylsilanolate (2.56 g, 20 mmol) in dry tetrahydrofuran (50 mL); a 4 h reaction time was used. Potassium diphenylphosphinate (4.46 g, 87% yield) was isolated as a white solid: $^1$H NMR (D$_2$O, DSS) δ 6.8–7.9 (m, Ar—$\underline{H}$'s, 10H). Anal. Calcd. for C$_{12}$H$_{10}$KO$_2$P: C, 56.24; H, 3.93; K, 15.26; P, 12.09. Found: C, 52.57, 52.49, 54.53, 54.38; H, 4.00, 4.09, 4.02, 4.36; K, 14.78; P, 11.01, 10.89.

EXAMPLE 31

Sodium diphenylphosphinate

The procedure of Example 1 was followed except that a mixture of phenyl diphenylphosphinate (13.76 g, 46.7 mmol), sodium trimethylsilanolate (5.6 g, 50 mmol), and dry tetrahydrofuran (175 mL) was left standing overnight (as it became impossible to stir). Sodium diphenylphosphinate (7.6 g, 68% yield) was isolated as a white solid: $^1$H NMR (D$_2$O) δ 6.6–8.0 (m, Ar—$\underline{H}$'s 10H). Anal. Calcd. for C$_{12}$H$_{10}$NaO$_2$P: C, 60.01; H, 4.20; P, 12.90. Found: C, 55.25, 55.47; H, 4.22, 4.20; P, 11.06, 11.15.

EXAMPLE 32

Potassium diethylphosphate

The procedure of Example 1 was followed except that triethylphosphate (3.4 mL, 20 mmol) was added by syringe to a slurry of potassium trimethylsilanolate (2.56 g, 20 mmol) in dry tetrahydrofuran (50 mL), and a 2 h reaction time at room temperature was used, followed by 40 h of heating at reflux. Potassium diethylphosphate (3.55 g, 92% yield) was isolated as a white solid: $^1$H NMR (D$_2$O, DSS) δ 1.1 (t, J=6.9 Hz, 6H), 3.75 (q, J=6.9 Hz, 4H). Anal. Calcd. for C$_4$H$_{10}$KO$_4$P: C, 25.00; H, 5.24; K, 20.34. Found: C, 25.83, 25.88; H, 5.40, 5.29; K, 20.37, 20.10.

EXAMPLE 33

Dipotassium perfluoro-2,4-dimethyl-3-oxa-1,5-pentanedioate

The procedure of Example 1 was followed using ~95% pure 4-carbomethoxyperfluoro-2-methyl-3-oxapentanoyl fluoride (12.5 g, 39 mmol), potassium trimethylsilanolate (10 g, 78 mmol), and dry ether (300 mL). Dipotassium perfluoro-2,4-dimethyl-3-oxa-1,5-pentanedioate (14.6 g, 98% yield) was isolated as a white solid: $^{19}$F NMR (D$_2$O) δ −78.8 (m, CF$_3$, 6F), −124.1 (m, C$\underline{F}$, 1F), −130.3 ppm (m, C$\underline{F}$, 1F). Anal. Calcd. for C$_6$F$_8$K$_2$O$_5$: C, 18.85; F, 39.76; K, 20.46. Found: C, 17.45; F, 37.65, 37.53; K, 21.50, 21.30.

EXAMPLE 34

Potassium methyl carbonate

The procedure of Example 1 was followed using dimethylcarbonate (3 mL, 35.6 mmol), potassium trimethylsilanolate (4.57 g, 35.6 mmol), dry ether (100 mL), and a 3 h reaction time. Potassium methyl carbonate (3.52 g, 87% yield) was isolated as a white solid: $^1$H NMR D$_2$O) δ 3.2 ppm (s, CH$_3$, 3H). Anal. Calcd. for C$_2$H$_3$KO$_3$: C, 21.04; H, 2.65; $\overline{K}$, 34.26. Found: C, 20.67; H, 2.71; K, 34.62.

EXAMPLE 35

Potassium ethyl oxalate

The procedure of Example 1 was followed using diethyl oxalate (3.0 mL, 22 mmol), potassium trimethylsilanolate (3.85 g, 22 mmol), dry ether (70 mL), an ice bath to maintain room temperature initially, and a 1.5 h reaction time. Potassium ethyl oxalate (2.72 g, 79% yield) was isolated as a white solid: $^1$H NMR (D$_2$O) δ 1.3 (t, J=7.2 Hz, C$\underline{H}_3$, 3H), 4.2 ppm (q, J=7.2 Hz, C$\underline{H}_2$, 2H). Anal. Calcd. for C$_4$H$_5$KO$_4$: C, 30.76; H, 3.23; K, 25.04. Found: C, 30.39; H, 3.29; K, 25.30.

EXAMPLE 36

Sodium perfluoropropionate

The procedure of Example 1 was followed using methyl perfluoropropionate (3 mL, 23.4 mmol), sodium trimethylsilanolate (2.63 g, 23.4 mmol), dry methylene chloride (100 mL), and a 1 h reaction time. Sodium perfluoropropionate (4.0 g, 92% yield) was obtained as a white solid: $^1$H NMR (D$_2$O) δ −82.4 (t, J=2 Hz, C$\underline{F}_3$, 3F), −120.1 ppm (q, J=2 Hz, C$\underline{F}_2$, 2F).

EXAMPLE 37

Potassium acetate

The procedure of Example 1 was followed using t-butyl acetate (4.0 mL, 30 mmol), potassium trimethylsilanolate (3.81 g, 30 mmol), dry ether (100 mL), and a 3 h reaction time. Potassium acetate (2.25 g, 77% yield) was isolated as a white solid: $^1$H NMR (D$_2$O) δ 1.8 ppm (s, C$\underline{H}_3$, 3H).

EXAMPLE 38

Polymeric Carboxylic Acid Salt

A mixture of potassium trimethylsilanolate (0.5 g, 4 mmol), a copolymer of ethylene and 2-methylene-1,3-dioxepane (MDO), prepared as described by W. J. Bailey and B. Gapud, Amer. Chem. Soc. Div. Polymer Chem., Preprints, 25 [1], 58 (1984), with $\overline{M}_n$ 19,000, $\overline{M}_w$ 42,600, 0.3 mol % MDO (1.5 g; contains 0.16 meq of MDO), and dry xylenes (50.0 mL) was heated at reflux for 4 days under nitrogen. Distilled water (0.20 mL) was then added to the reaction mixture before cooling it to 80° and pouring it into cold methanol (200 mL). The resulting precipitate was filtered off and divided into two approximately equal portions.

The first portion of solid was washed with 7.8 mM potassium hydroxide in methanol (3×10 mL) and 3.9 mM potassium hydroxide in methanol (10 mL) before drying it overnight under vacuum (0.1 mm) at 50°. The resulting solid (0.38 g) showed the expected infrared stretching frequency for a carboxylate anion at 1569 cm$^{-1}$, confirming that the ester function in the polymer was cleaved.

The second portion of solid was washed with 1% hydrochloric acid in methanol (3×10 mL), distilled water (3×10 mL), and cold methanol (2×10 mL) before drying it overnight under vacuum (0.1 mm) at 50°. The resulting solid (0.51 g) showed the expected infrared stretching frequency for a carboxylic acid carbonyl group at 1711 cm$^{-1}$, confirming that the ester function in the polymer was cleaved.

BEST MODE FOR CARRYING OUT THE INVENTION

The best mode presently contemplated for carrying out the process of the invention is illustrated by Examples 2, 8, 12, 20, 22, 29 and 33.

Although preferred embodiments of the invention have been disclosed herein, it is to be understood that there is no intent to limit the invention to the precise constructions so disclosed, and that the right is reserved to all changes and modifications coming within the scope of the invention as defined in the appended claims.

INDUSTRIAL APPLICABILITY

The invention process provides carboxylic acid salts which find utility in a wide variety of commercial applications, for example, as detergents and surfactants, ion-exchange compounds, intermediates to fluoroolefin monomers used to make fluorinated polymers having plastic, elastomeric and ion-exchange properties, and as pharmaceutical intermediates and end-products.

What is claimed is:

1. One-step process for preparing anhydrous, organic acid alkali or alkaline earth metal salts by contacting and reacting in an anhydrous inert atmosphere, at a temperature of about −80° to about 200° C. the organic compound of the formula R(ZX)$_k$ and the organic alkali metal or alkaline earth metal silanolate of the formula [(R$^1$)(R$^2$)(R$^3$)SiO]$_n$M wherein:

each Z, independently, is

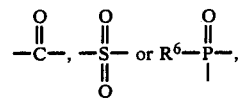

each X, independently, is the monovalent leaving group F or OR$^5$, or: (i)

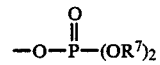

when Z is

or (ii)

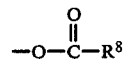

when Z is

M is alkali or alkaline earth metal;
   n is 1 or 2;
   k is 1, 2 or 3;
   R is selected from a connecting bond, R$^4$ and OR$^4$ wherein R$^4$ is an aliphatic, unsaturated aliphatic, fluorinated aliphatic, alicyclic, aromatic or aliphatic-aromatic hydrocarbon radical which contains up to 30 carbon atoms and which is of valence k;
   each of R$^1$, R$^2$, and R$^3$ is independently selected from H, provided at least one of these groups is not H, C$_{1-10}$ alkyl, C$_{1-10}$ oxyalkyl and C$_{6-10}$ aryl and alkaryl;
   each R$^5$, independently, is a C$_{1-30}$ alkyl or fluorinated alkyl, C$_{2-30}$ alkenyl or alkynyl, C$_{3-8}$ cycloalkyl, or C$_{6-30}$ aryl, aralkyl or alkaryl radical;

each $R^6$, independently, is $R^7$ or $OR^7$;
each $R^7$, independently, is $C_{1-20}$ alkyl or $C_{6-20}$ aryl, alkaryl or aralkyl; and
each $R^8$, independently, is $C_{1-12}$ alkyl.

2. Process of claim 1 wherein Z is

and the monovalent leaving group X is $OR^5$.

3. Process of claim 2 wherein each $R^5$, independently, is $C_{1-12}$ alkyl or $C_{6-12}$ aryl or aralkyl.

4. Process of claim 3 wherein each of $R^1$, $R^2$ and $R^3$ is independently selected from $C_{1-3}$ alkyl.

5. Process of claim 4 wherein each of $R^1$, $R^2$ and $R^3$ is methyl.

6. Process of claim 1 wherein Z is

and the monovalent leaving group X is F.

7. Process of claim 6 wherein each of $R^1$, $R^2$ and $R^3$ is independently selected from $C_{1-3}$ alkyl.

8. Process of claim 7 wherein each of $R^1$, $R^2$ and $R^3$ is methyl.

9. Process of claim 1 wherein Z is

and the monovalent leaving group X is F.

10. Process of claim 9 wherein each of $R^1$, $R^2$ and $R^3$ is independently selected from $C_{1-3}$ alkyl.

11. Process of claim 10 wherein each of $R^1$, $R^2$ and $R^3$ is methyl.

12. Process of claim 1 wherein Z is

and the monovalent leaving group X is $OR^5$.

13. Process of claim 12 wherein each $R^5$, independently, is $C_{1-12}$ alkyl or $C_{6-12}$ aryl or aralkyl and $R^6$ is $OR^7$ wherein $R^7$ is $C_{1-10}$ alkyl.

14. Process of claim 13 wherein each of $R^1$, $R^2$ and $R^3$ is independently selected from $C_{1-3}$ alkyl.

15. Process of claim 14 wherein each of $R^1$, $R^2$ and $R^3$ is methyl.

16. Process of claim 1 wherein Z is

and the monovalent leaving group X is F.

17. Process of claim 16 wherein $R^6$ is $OR^7$ wherein $R^7$ is $C_{1-10}$ alkyl.

18. Process of claim 17 wherein each of $R^1$, $R^2$ and $R^3$ is methyl.

19. Process of claim 1 wherein Z is

and the monovalent leaving group X is

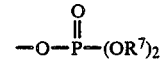

wherein $R^7$ is $C_{1-10}$ alkyl.

20. Process of claim 19 wherein each of $R^1$, $R^2$ and $R^3$ is methyl.

21. Process of claim 1 wherein M is an alkali metal.

22. Process of claim 4 wherein k is 2, R is a connecting bond and each $R^5$, independently, is $C_{1-12}$ alkyl.

23. Process of claim 4 wherein R is $R^4$ or $OR^4$, $R^4$ is $C_{1-12}$ fluorinated alkyl and each $R^5$, independently, is $C_{1-12}$ alkyl.

24. Process of claim 23 wherein $R^4$ contains ether oxygen.

25. Process of claim 5 wherein R is $R^4$, $R^4$ is 3-pyridyl or 2-furyl and $R^5$ is methyl.

26. Process of claim 2 wherein R is $R^4$, $R^4$ is $C_{6-10}$ aryl and each $R^5$, independently, is $C_{1-12}$ alkyl or $C_{6-12}$ aryl or aralkyl.

27. Process of claim 26 wherein $R^4$ is substituted with one or more functional groups that are inert under reaction conditions.

28. Process of claim 26 wherein each $R^5$, independently, is methyl, phenyl or benzyl and each of $R^1$, $R^2$ and $R^3$ is methyl.

29. Process of claim 10 wherein R is $R^4$ and $R^4$ is $C_{1-12}$ fluorinated alkyl containing ether oxygen.

30. Process of claim 1 wherein Z is

k is 2, R is $R^4$, $R^4$ is fluorinated aliphatic of valence k and containing ether oxygen, and the monovalent leaving group X is F or $OR^5$ wherein $R^5$ is methyl.

31. Process of claim 1 wherein Z is

R is $R^4$, $R^4$ is $C_{1-12}$ alkyl, and the monovalent leaving group X is

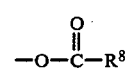

wherein $R^8$ is $C_{1-4}$ alkyl.

32. Process of claim 1 wherein the temperature range is about 10° C. to about 120° C.

33. Process of claim 1 carried out in the presence of an inert dry solvent wherein the reactants are at least partly soluble.

34. Process of claim 1 wherein $R^4$ contains ether oxygen, thioether sulfur or tertiary nitrogen.

35. Process of claim 1 wherein $R^4$ contains one or more functional substituents that are inert under reaction conditions.

36. Process of claim 1 wherein $R^5$, except $C_{6-30}$ aryl, aralkyl or alkaryl, contains ether oxygen, thioether sulfur or tertiary nitrogen.

37. Process of claim 1 wherein $R^5$, except $C_{6-30}$ aryl, aralkyl or alkaryl, contains one or more functional substituents that are inert under reaction conditions.

* * * * *